(12) United States Patent
Sonesson et al.

(10) Patent No.: US 8,586,572 B2
(45) Date of Patent: Nov. 19, 2013

(54) 3-PHENYL-AZETIDINE DERIVATIVES USEFUL AS MODULATORS OF CORTICAL CATECHOLAMINERGIC NEUROTRANSMISSION

(75) Inventors: Clas Sonesson, Billdal (SE); Lars Swanson, Öjersjö (SE); Fredrik Pettersson, Göteborg (SE)

(73) Assignee: Integrative Research Laboratories Sweden AB, Gothenburg (SE)

( * ) Notice: Subject to any disclaimer, the term of this patent is extended or adjusted under 35 U.S.C. 154(b) by 200 days.

(21) Appl. No.: 13/130,384

(22) PCT Filed: Nov. 24, 2009

(86) PCT No.: PCT/EP2009/065675
§ 371 (c)(1), (2), (4) Date: Jul. 7, 2011

(87) PCT Pub. No.: WO2010/058017
PCT Pub. Date: May 27, 2010

(65) Prior Publication Data
US 2011/0281835 A1     Nov. 17, 2011

Related U.S. Application Data

(60) Provisional application No. 61/117,818, filed on Nov. 25, 2008.

(30) Foreign Application Priority Data

Nov. 24, 2008  (DK) ................................ 2008 01656

(51) Int. Cl.
*C07D 205/04* (2006.01)
*A61K 31/397* (2006.01)

(52) U.S. Cl.
USPC ..................................... 514/210.01; 548/952

(58) Field of Classification Search
None
See application file for complete search history.

(56) References Cited

U.S. PATENT DOCUMENTS

| | | | |
|---|---|---|---|
| 3,481,920 A | 12/1969 | Hargrove | |
| 3,494,964 A | 2/1970 | Hargrove | |
| 3,668,196 A | 6/1972 | Hargrove | |
| 3,822,252 A | 7/1974 | Gold | |
| 7,579,474 B2 | 8/2009 | Sonesson et al. | |
| 2005/0096308 A1 | 5/2005 | Ellsworth et al. | |
| 2005/0143372 A1 | 6/2005 | Ghosh et al. | |
| 2007/0275930 A1 | 11/2007 | Gentles et al. | |
| 2010/0179211 A1 | 7/2010 | Sonesson et al. | |
| 2010/0197760 A1 | 8/2010 | Sonesson et al. | |
| 2011/0257148 A1 | 10/2011 | Sonesson et al. | |
| 2011/0257241 A1 | 10/2011 | Sonesson et al. | |
| 2011/0257242 A1 | 10/2011 | Sonesson et al. | |

FOREIGN PATENT DOCUMENTS

| | | |
|---|---|---|
| GB | 1236078 | 6/1971 |
| GB | 1266587 | 3/1972 |
| WO | WO 03/037271 A2 | 5/2003 |
| WO | WO 2005/026153 A1 | 3/2005 |
| WO | WO 2005/121092 A1 | 12/2005 |
| WO | WO 2006/134487 A1 | 12/2006 |
| WO | WO 2007/140200 A2 | 12/2007 |
| WO | WO 2008/148801 A2 | 12/2008 |

OTHER PUBLICATIONS

Hörig et al., J. Translational Med. 2:44 (2004).*
Depoortere, et al., Neuropsychopharmacology, 28:1889, 1899 (2003).*
Brown et al., "New functionalised silicas for highly selective cation exchange SPE purification in medicinal chemistry," Tetrahedron Letters, vol. 49, 2008, pp. 4968-4971, XP-22819131A.

* cited by examiner

Primary Examiner — Michael Barker
(74) Attorney, Agent, or Firm — Birch, Stewart, Kolasch & Birch, LLP

(57) ABSTRACT

The present invention relates to novel 3-phenyl-azetidine derivatives, useful for modulating extracellular levels of catecholamines, dopamine and norepinephrine, in cerebral cortical areas of the mammalian brain, and more specifically for the treatment of central nervous system disorders. In other aspects the invention relates to pharmaceutical compositions comprising the 3-phenyl-azetidine derivatives of the invention and to the use of these compounds for therapeutic applications.

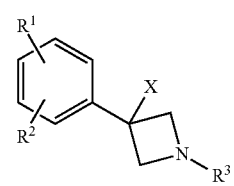

(1)

11 Claims, No Drawings

3-PHENYL-AZETIDINE DERIVATIVES USEFUL AS MODULATORS OF CORTICAL CATECHOLAMINERGIC NEUROTRANSMISSION

This application is the National Phase of PCT/EP2009/065675 filed on Nov. 24, 2009, which claims priority under 35 U.S.C. 119(e) to U.S. Provisional Application No. 61/117,818 filed on Nov. 25, 2008, and under U.S.C. 119(a) to Patent Application No. PA 2008 01656 filed in Denmark on Nov. 24, 2008, all of which are hereby expressly incorporated by reference into the present application.

FIELD OF THE INVENTION

The present invention relates to novel 3-phenyl-azetidine derivatives, useful for modulating extracellular levels of catecholamines, dopamine and norepinephrine, in cerebral cortical areas of the mammalian brain, and more specifically for the treatment of central nervous system disorders.

In other aspects the invention relates to pharmaceutical compositions comprising the 3-phenyl-azetidine derivatives of the invention and to the use of these compounds for therapeutic applications.

BACKGROUND OF THE INVENTION

The cerebral cortex encompasses several major regions that are involved in higher functions such as thought, feelings, memory and planning. Biogenic amines, i.e. dopamine, norepinephrine and serotonin, are important for mammalian cortical function. The ascending dopamine and norepinephrine pathways innervate the cortex. The serotonergic neurons of the CNS project to virtually all regions of the brain including the cerebral cortex. Primary or secondary dysfunctions in the activity of these pathways lead to dysregulation of the activity at dopamine and norepinephrine and serotonin receptors in these brain areas and subsequently to manifestations of psychiatric and neurological symptoms.

The biogenic amines of the cortex modulate several aspects of cortical functions controlling affect, anxiety, motivation, cognition, attention, arousal and wakefulness. Thus, the catecholamines dopamine and norepinephrine exert strong influence on the prefrontal cortical areas, the integrity of which is essential for the so-called executive cognitive functions, related to e.g. attention, planning of actions and impulse control. Norepinephrine is a major part in the circuitry regulating anxiety and fear and is thus believed to be dysregulated in anxiety disorders such as panic disorders, generalized anxiety disorder (GAD) and specific phobias. Concerning mood and affective functions, the usefulness of compounds facilitating particularly norepinephrine and serotonin neurotransmission in the treatment of depression and anxiety has strongly contributed to the widely-accepted concept that these neurotransmitters are both involved in the regulation of affective functions.

In general, compounds specifically affecting the transmission of biogenic amines, more precisely monoamines, norepinephrine, dopamine and serotonin are successfully used to alleviate the affective, cognitive, or attentional symptoms in patients suffering from e.g. depression, anxiety and attention deficit hyperactivity disorders (ADHD).

Furthermore, the monoamine systems in the cortex are known to be directly or indirectly involved in the core symptoms of schizophrenia. Based on a synthesis of biochemical and genetic findings along with neuropyschological observations indicating dysfunction of specific cortical areas in schizophrenia, it has been proposed that this disorder emerges as various pathological etiologies converge upon cortical function leading to dysregulation of the cortical micro-circuitry, which is clinically manifested as the symptoms of schizophrenia. This cortical micro-circuitry is regulated by several neurotransmitters, including glutamate, GABA, and dopamine.

GB 1266587 describes certain azetidinol derivatives useful as analgesic drugs, GB 1236078 describes certain substituted azetidinols useful as antidepressants, and U.S. Pat. Nos. 3,481,920, 3,494,964 and 3,668,196 describe certain substituted azetidinol derivatives useful as CNS stimulants. However, the 3-phenyl-azetidine derivatives of the present invention are not reported.

SUMMARY OF THE INVENTION

The object of the present invention is to provide novel pharmaceutically active compounds, especially useful in treatment of disorders in the central nervous system. A further object is the provision of compounds for modulation of dopamine and norepinephrine neurotransmission in the mammalian brain, including human brain. A still further object is the provision of novel compounds with a cortical enhancer profile. A further object is to provide compounds with therapeutic effects after oral administration. A still further object is the provision of compounds with more optimal pharmacodynamic properties such as e.g. kinetic behaviour, bioavailability, solubility and efficacy. A further object is to provide compounds being superior to presently known compounds in the treatment of several disorders related to dysfunctions of the CNS, in terms of efficacy or side effects.

The present invention concerns the unexpected discovery of the pharmacological effects of compounds of the invention on monoamines in the cerebral cortex, and the use of these compounds in the treatment for certain CNS disorders. By pharmacological testing in vivo in the rat it is demonstrated that compounds of the present invention produce regionally selective increases in catecholamine levels in the frontal cortex. Due to the specific modulatory effects of the catecholamines on cortical functions related to cognition, attention and affect, the compounds of the invention can be used in the treatment of disorders characterised by dysfunctions in these areas. Thus, the compounds can be used in the treatment of cognitive disorders, ADHD, depression, and anxiety. The compounds can also be used to treat schizophrenia, which is characterised by dysfunctions of the cerebral cortex manifested in cognitive failure and psychosis.

In its first aspect, the invention provides a compound of Formula 1

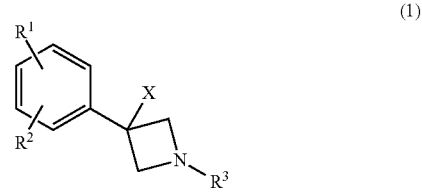

(1)

any of its stereoisomers or any mixture of its stereoisomers, or an N-oxide thereof, or a deuterated analog thereof, or a pharmaceutically acceptable salt thereof; wherein $R^1$, $R^2$, $R^3$ and X are as defined below.

In its second aspect, the invention provides a pharmaceutical composition, comprising a therapeutically effective amount of a compound of the invention, any of its stereoisomers or any mixture of its stereoisomers, or an N-oxide thereof, or a pharmaceutically acceptable salt thereof, together with at least one pharmaceutically acceptable carrier, excipient or diluent.

In a further aspect, the invention provides the use of a compound of the invention, any of its stereoisomers or any mixture of its stereoisomers or an N-oxide thereof, or a pharmaceutically acceptable salt thereof, for the manufacture of a pharmaceutical composition for the treatment, prevention or alleviation of a disease or a disorder or a condition of a mammal, including a human, which disease, disorder or condition is responsive to responsive to modulation of catecholamines in the cerebral cortex.

In a still further aspect, the invention relates to a method for treatment, prevention or alleviation of a disease or a disorder or a condition of a living animal body, including a human, which disorder, disease or condition is responsive to modulation of catecholamines in the cerebral cortex, which method comprises the step of administering to such a living animal body in need thereof a therapeutically effective amount of a compound of the invention, any of its stereoisomers or any mixture of its stereoisomers, or an N-oxide thereof, or a pharmaceutically acceptable salt thereof.

Other aspects of the invention will be apparent to the person skilled in the art from the following detailed description and examples.

DETAILED DESCRIPTION OF THE INVENTION

3-Phenyl-azetidine Derivatives

In its first aspect the present invention provides a 3-phenyl-azetidine derivative represented by Formula 1:

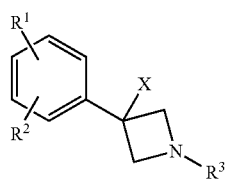

(1)

any of its stereoisomers or any mixture of its stereoisomers, or an N-oxide thereof, or a deuterated analog thereof, or a pharmaceutically acceptable salt thereof, wherein X is OH or $OCH_3$;
$R^1$ is F or Cl;
$R^2$ is H, F or Cl;
$R^3$ is H, $CH_3$ or $CH_2CH_3$;
and with the proviso that if X is OH, then $R^3$ is not H.

In a preferred embodiment, 3-phenyl-azetidine derivative of the invention is a compound of Formula 2,

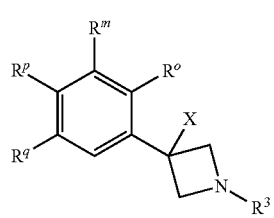

(2)

any of its stereoisomers or any mixture of its stereoisomers, or an N-oxide thereof, or a deuterated analog thereof, or a pharmaceutically acceptable salt thereof, wherein one of $R^o$, $R^m$, $R^p$ and $R^q$ represents $R^1$;
one the remaining three of $R^o$, $R^m$, $R^p$ and $R^q$ represents $R^2$;
the two remaining of $R^o$, $R^m$, $R^p$ and $R^q$ represent H; and
X and $R^3$ are as defined above.

In a more preferred embodiment, $R^m$ represents $R^1$; $R^o$ represents $R^2$; and $R^p$ and $R^q$ represent H.

In a further embodiment, $R^m$ represents $R^1$; $R^p$ represents $R^2$; and $R^o$ and $R^q$ represent H.

In a still further embodiment, $R^m$ represents $R^1$; $R^q$ represents $R^2$; and $R^o$ and $R^p$ represent H.

In another preferred embodiment, 3-phenyl-azetidine derivative of the invention is a compound of Formula 1 or Formula 2, any of its stereoisomers or any mixture of its stereoisomers, or an N-oxide thereof, or a deuterated analog thereof, or a pharmaceutically acceptable salt thereof, wherein X is OH or $OCH_3$.

In a more preferred embodiment, X is OH.

In another more preferred embodiment, X is $OCH_3$.

In a third preferred embodiment, 3-phenyl-azetidine derivative of the invention is a compound of Formula 1 or Formula 2, any of its stereoisomers or any mixture of its stereoisomers, or an N-oxide thereof, or a deuterated analog thereof, or a pharmaceutically acceptable salt thereof, wherein $R^1$ is F or Cl.

In a more preferred embodiment, $R^1$ is F.

In another more preferred embodiment, $R^1$ is Cl.

In a fourth preferred embodiment, 3-phenyl-azetidine derivative of the invention is a compound of Formula 1 or Formula 2, any of its stereoisomers or any mixture of its stereoisomers, or an N-oxide thereof, or a deuterated analog thereof, or a pharmaceutically acceptable salt thereof, wherein $R^2$ is H, F or Cl.

In a more preferred embodiment, $R^2$ is H.

In another more preferred embodiment, $R^2$ is F.

In a third more preferred embodiment, $R^2$ is Cl.

In a fifth preferred embodiment, 3-phenyl-azetidine derivative of the invention is a compound of Formula 1 or Formula 2, any of its stereoisomers or any mixture of its stereoisomers, or an N-oxide thereof, or a deuterated analog thereof, or a pharmaceutically acceptable salt thereof, wherein $R^3$ is H, $CH_3$ or $CH_2CH_3$, or a deuterated analog thereof.

In a more preferred embodiment, $R^3$ is H or D.

In another more preferred embodiment, $R^3$ is $CH_3$ or $CD_3$.

In a third more preferred embodiment, $R^3$ is $CH_3$.

In a fourth more preferred embodiment, $R^3$ is $CH_2CH_3$ or $CD_2CD_3$.

In a fifth more preferred embodiment, $R^3$ is $CH_2CH_3$.

In yet another more preferred embodiment, 3-phenyl-azetidine derivative of the invention is 3-(2,3-Difluorophenyl)-1-ethylazetidin-3-ol;
3-(3,4-Difluorophenyl)-1-ethylazetidin-3-ol;
3-(3,5-Difluorophenyl)-1-ethylazetidin-3-ol;
3-(3-Chloro-5-fluorophenyl)-1-ethylazetidin-3-ol;
3-(3,4-Difluorophenyl)-1-(ethyl-D5)azetidin-3-ol;
3-(3-Chloro-2-fluorophenyl)-1-ethylazetidin-3-ol;
3-(2,3-Difluorophenyl)-1-ethylazetidin-3-ol-1-oxide;
3-(2,3-Difluorophenyl)-3-methoxyazetidine;
3-(2,3-Difluorophenyl)-1-ethyl-3-methoxyazetidine; or
3-(2,3-Difluorophenyl)-1-(ethyl-D5)azetidin-3-ol;

any of its stereoisomers or any mixture of its stereoisomers, or an N-oxide thereof, or a deuterated analog thereof, or a pharmaceutically acceptable salt thereof.

In still another more preferred embodiment, 3-phenyl-azetidine derivative of the invention is 3-(2,3-Difluorophenyl)-1-ethylazetidin-3-ol;

any of its stereoisomers or any mixture of its stereoisomers, or an N-oxide thereof, or a deuterated analog thereof, or a pharmaceutically acceptable salt thereof.

In a further more preferred embodiment, 3-phenyl-azetidine derivative of the invention is 3-(2,3-Difluorophenyl)-1-ethylazetidin-3-ol fumaric acid salt;

any of its stereoisomers or any mixture of its stereoisomers, or an N-oxide thereof, or a deuterated analog thereof.

Any combination of two or more of the embodiments as described above is considered within the scope of the present invention.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may exist in different stereoisomeric forms—including enantiomers, diastereomers or cis-trans-isomers.

The invention includes all such isomers and any mixtures thereof including racemic mixtures.

Racemic forms can be resolved into the optical antipodes by known methods and techniques. One way of separating the enantiomeric compounds (including enantiomeric intermediates) is—in the case the compound being a chiral acid—by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

N-Oxides

In the context of this invention an N-oxide designates an oxide derivative of a tertiary amine, including a nitrogen atom of an aromatic N-heterocyclic compound, a non-aromatic N-heterocyclic compounds, a trialkylamine and a trialkenylamine. For example, the N-oxide of a compound containing a pyridyl may be the 1-oxy-pyridin-2, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Deuterated Analogs

The compounds of the invention may be provided in the form of their deuterated analogs. Deuterium forms bonds with carbon that vibrate at a lower frequency and are thus stronger than C—H bonds. Therefore "heavy hydrogen" (deuterium) versions of drugs may be more stable towards degradation and last longer in the organism.

The deuterated analog of the invention may be a fully or partially deuterium substituted derivative. Preferably the deuterium substituted derivative of the invention holds a fully or partially deuterium substituted alkyl group, and in particular —$CD_3$ (methyl-D3) or —$CD_2CD_3$ (ethyl-D5).

In the context of this invention, when a particular position is designated as holding deuterium (stated as "D" or "deuterium"), it is understood that the abundance of deuterium at that position is substantially greater than the natural abundance of deuterium, which is 0.015% (i.e., at least 50.1% incorporation of deuterium).

In a preferred embodiment the abundance of deuterium at that position is at least 3340 times greater (i.e. at least 50.1% incorporation of deuterium) than the natural abundance of deuterium, which is 0.015%. In other preferred embodiments of the invention the abundance of deuterium at that position is at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Persons skilled in the art will appreciate that, in order to obtain compounds of the invention in an alternative—and in some occasions, more convenient manner—the individual process steps mentioned hereinbefore may be performed in a different order, and/or the individual reactions may be performed at different stage in the overall route (i.e. chemical transformations may be performed upon different intermediates to those associated hereinbefore with a particular reaction).

Biological Activity

The compounds according to the present invention possess norepinephrine, dopamine and to some extent serotonin-modulating properties and both they and their pharmaceutical compositions are useful in treating numerous central nervous system disorders including psychiatric disorders. Particularly, the compounds and their pharmaceutical compositions are used in the treatment of CNS disorders where the cortical monoaminergic systems are dysfunctional due to direct or indirect causes. In a further embodiment, the compounds according to the present invention can be used to treat affective disorders and cognitive disorders including neurodegenerative and developmental disorders. Also, compounds with modulating effects on dopaminergic systems may also be used to improve motor and cognitive functions.

In a special embodiment, the compounds of the invention are considered useful for the treatment, prevention or alleviation of dementia, age-related cognitive impairment, Autism spectrum disorders, ADHD, Cerebral Palsy, Huntington's disease, Gilles de la Tourette's syndrome, depression, bipolar disorder, schizophrenia, schizophreniform disorders, generalized anxiety disorder (GAD), specific phobias, panic disorder, sleep disorders, bipolar disorders, drug induced psychotic disorders, iatrogenic psychoses, Iatrogenic hallucinoses, non-iatrogenic psychoses, non-iatrogenic hallucinoses, mood disorders, anxiety disorders, depression, obsessive-compulsive disease, emotional disturbances related to ageing, Alzheimer's disease, dementia, dementia disorders related to Alzheimer's disease, age-related cognitive impairment, brain injury, substance abuse, disorders characterized by misuse of food, sleep disorders, sexual disorders, eating disorders, obesitas, headaches, pains in conditions characterized by increased muscular tone, movement disorders, Parkinson's disease, Parkinsonism, parkinsonian syndromes, dyskinesias, L-DOPA induced dyskinesias, dystonias, neurodevelopmental disorders, neurodegenerative disorders, tics, tremor, restless legs, narcolepsy and behavioural disorders.

Pharmaceutical Compositions

In another aspect the invention provides novel pharmaceutical compositions comprising a therapeutically effective amount of the chemical compound of the invention.

The present invention relates to pharmaceutical compositions comprising the compounds of the present invention, and their use in treating CNS disorders. Both organic and inorganic acids can be employed to form non-toxic pharmaceutically acceptable acid addition salts of the compounds according to the invention. Suitable acid addition salts of the compounds of the present invention include those formed with pharmaceutically acceptable salts such as those mentioned above. The pharmaceutical composition comprising a compound according to the invention may also comprise substances used to facilitate the production of the pharmaceutical preparation or the administration of the preparations. Such substances are well known to people skilled in the art and may for instance be pharmaceutically acceptable adjuvants, carriers and preservatives.

In clinical practice, the compounds according to the present invention will normally be administered orally, rectally, nasally or by injection, in the form of pharmaceutical preparations comprising the active ingredient either as a free base or as a pharmaceutically acceptable non-toxic, acid addition salt, such as the hydrochloride, lactate, acetate or sulfamate salt, in association with a pharmaceutically acceptable carrier. The carrier may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing the compound according to the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinyl-pyrrolidine, and a lubricant such as magnesium stearate, calcium stearate, polyethylene glycol, waxes, paraffin, and the like, and then compressed into tablets. If coated tablets are required, the cores (prepared as described above) may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Examples of tablet and capsule formulations suitable for oral administration are given below:

| Tablet I | mg/tablet |
|---|---|
| Compound | 100 |
| Lactose Ph. Eur | 182.75 |
| Croscarmellose sodium | 2.0 |
| Maize starch paste (5% w/v paste) | 2.25 |
| Magnesium stearate | 3.0 |

| Tablet II | mg/tablet |
|---|---|
| Compound | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| Tablet III | mg/tablet |
|---|---|
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| Capsule | mg/capsule |
|---|---|
| Compound | 10 |
| Lactose Ph. Eur | 488.5 |
| Magnesium | 1.5 |

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain coloring agents, flavoring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also containing stabilizing agents and/or buffering agents and may conveniently be provided in various dosage unit ampoules. The use and administration to a patient to be treated would be readily apparent to an ordinary skill in the art.

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. The compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve that delivers a measured amount of active compound.

The compounds of the invention may also be administered in a controlled release formulation. The compounds are released at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. The compounds may also be formulated in controlled release formulations in which release of the active compound is targeted. For example, release of the compound may be limited to a specific region of the digestive system through the pH sensitivity of the formulation. Such formulations are well known to persons skilled in the art.

Further details on techniques for formulation and administration may be found in the latest edition of Remington's Pharmaceutical Sciences (Maack Publishing Co., Easton, Pa.).

Depending upon the disorder and patient to be treated and the route of administration, the compositions may be administered at varying doses. The dosing will also depend upon the relation of potency to absorbability and the frequency and route of administration. Such doses may be administered once, twice or three or more times daily. The compounds of this invention can be administered to subjects in doses ranging from 0.01 mg to 500 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for

EXAMPLES

The invention is further illustrated in the examples below, which in no way are intended to limit the scope of the invention.

Example 1

3-(2,3-difluorophenyl)-1-ethylazetidin-3-ol 1,3-dichloro-2-(2,3-difluorophenyl)propan-2-ol (6.0 g, 24.89 mmol) was dissolved in acetonitrile (90 ml) and transferred to 6 different microwave vials where each vial contained equal amounts (1.0 g, 2.49 mmol). In each tube sodium bicarbonate (1.04 g, 12.44 mmol (in total 6.27 g, 74.67 mmol)) was added and the tubes were sealed. Through the septum ethylamine in tetrahydrofurane (2.0 M, 2.07 ml, 4.15 mmol (in total 12.44 ml, 24.89 mmol) was added and the mixture was heated at 120° C. for 30 min under microwave irradiation. Additional ethylamine in tetrahydrofurane (2.0 M, 1.03 ml, 2.07 mmol (in total 6.22 ml, 12.44 mmol) was added and the mixture was heated at 120° C. for 30 min under microwave irradiation. The solutions where pooled, water (100 ml) and tert-butyl methyl ether (100 ml) was added and the organic phase was collected. The aqueous phase was extracted with tert-butyl methyl ether (100 ml), the pooled organic phase was dried ($Na_2SO_4$) and evaporated. The crude product was purified by flash column chromatography on silica gel (ethyl acetate/methanol, 1:0 to 9:1) to give the title compound (2.53 g, 48%). The amine was converted to the fumaric acid salt and recrystallized from ethanol/diethyl ether/diisopropyl ether: M.p. 148-150° C. MS m/z (relative intensity, 70 eV) 213 (M+, 1), 156 (39), 141 (75), 127 (56), 58 (bp).

Example 2

3-(3,4-difluorophenyl)-1-ethylazetidin-3-ol

A mixture of 3-(3,4-difluorophenyl)azetidin-3-ol (0.3 g, 1.62 mmol) triethylamine (0.68 ml, 4.87 mmol) and iodoethane (0.19 ml, 2.44 mmol) in tetrahydrofuran (15 ml) was stirred at ambient temperature for 15 h. The solvent was evaporated and aqueous hydrochloric acid (50 mL. 10%) was added and the mixture was washed with tert-butyl methyl ether (2×50 ml). The aqueous phase was made basic by addition of aqueous sodium hydroxide (5 M) and extracted with tert-butyl methyl ether (2×50 ml). The combined organic phase was dried ($Na_2SO_4$) and evaporated under reduced pressure to give the crude product (0.26 g). Purification by flash column chromatography on silica gel (ethyl acetate/methanol 1:1) gave 0.2 g (58%) of the title compound. The amine was converted to the fumaric acid salt and recrystallized from methanol/diethyl ether: M.p. 177-179° C. MS m/z (relative intensity, 70 eV) 213 (M+, 1), 141 (86), 127 (45), 114 (58), 58 (bp).

Example 3

3-(3,5-difluorophenyl)-1-ethylazetidin-3-ol 1,3-dichloro-2-(3,5-difluorophenyl)propan-2-ol (1.0 g, 4.15 mmol) was dissolved in acetonitrile (10 ml) and sodium bicarbonate (1.39 g, 16.59 mmol and ethylamine in water (70%, 0.33 ml, 4.15 mmol) was added and the mixture was refluxed for 10 h. Water (50 ml) and tert-butyl methyl ether (50 ml) was added and the organic phase was collected. The aqueous phase was extracted with tert-butyl methyl ether (50 ml, the pooled organic phase was extracted with aqueous hydrochloric acid (10%, 50 ml). The aqueous phase was basified and extracted with tert-butyl methyl ether (2×50 ml), dried ($Na_2SO_4$) and evaporated to give 0.35 g crude product. Purification by flash column chromatography on silica gel (ethyl acetate/MeOH 1:0→1:1) gave the title compound (0.2 g, 23%). The amine was converted to the fumaric acid salt and recrystallized from ethanol/diethyl ether/diisopropyl ether: M.p. 140-141° C. MS m/z (relative intensity, 70 eV) 213 (M+, 1), 156 (36), 141 (37), 127 (64), 114(50), 58 (bp).

Example 4

3-(3-chloro-5-fluorophenyl)-1-ethylazetidin-3-ol

A mixture of 3-(3-chloro-5-fluorophenyl)azetidin-3-ol (0.41 g, 2.03 mmol), potassium carbonate (0.56 g, 4.06 mmol) and iodoethane (0.31 g, 2.03 mmol) in acetonitrile (5 ml) was heated at 120° C. under microwave irradiation for 10 min. Water (50 ml) and ethyl acetate (50 ml) was added and the organic phase was collected. The aqueous phase was extracted with ethyl acetate (2×50 ml). The combined organic phase was dried ($Na_2SO_4$) and evaporated under reduced pressure to give the crude product. Purification by flash column chromatography on silica gel (ethyl acetate) gave 0.28 g (60%) of the title compound. The amine was converted to the fumaric acid salt and recrystallized from ethanol/diethyl ether/diisopropyl ether: M.p. 166-168° C. MS m/z (relative intensity, 70 eV) 229 (M+, 1), 172 (23), 130 (24), 109 (33), 58 (bp).

Example 5

3-(3,4-difluorophenyl)-1-(ethyl-D5)azetidin-3-ol

A mixture of 3-(3,4-difluorophenyl)azetidin-3-ol (0.02 g, 0.11 mmol), potassium carbonate (0.037 g, 0.27 mmol) and iodoethane-d5 (0.017 g, 0.11 mmol) in acetonitrile (5 ml) was heated at 120° C. under microwave irradiation for 30 min. The crude product was analyzed by GCMS. Analysis showed 30% conversion. MS m/z (relative intensity, 70 eV) 218 (M+, 1), 141 (58), 127 (31), 114 (39), 63 (bp).

Example 6

3-(3-chloro-2-fluorophenyl)-1-ethylazetidin-3-ol

A mixture of 1,3-dichloro-2-(3-chloro-2-fluorophenyl)propan-2-ol (0.88 g, 3.42 mmol), sodium bicarbonate (0.92 g, 10.95 mmol) and ethylamine in tetrahydrofurane (2.0 M, 1.82 ml, 3.64 mmol) in acetonitrile (15 ml) was heated at 120° C. for 30 min under microwave irradiation. Additional ethylamine in tetrahydrofurane (2.0 M, 0.91 ml, 1.82 mmol was added and the mixture was heated at 120° C. for 30 min under microwave irradiation. Aqueous sodium carbonate (50 ml, 10%) and ethyl acetate (50 ml) was added and the organic phase was collected. The aqueous phase was extracted with ethyl acetate (50 ml), the pooled organic phase was dried (MgSO4) and evaporated. The crude product was purified by flash column chromatography on silica gel (ethyl acetate/isooctane, 1:4 to 1:1) to give the title compound (0.28 g, 35%). The amine was converted to the fumaric acid salt and recrystallized from ethanol/diethyl ether/diisopropyl ether: M.p. 172-173° C. MS m/z (relative intensity, 70 eV) 229 (M+, 1), 172 (29), 157 (56), 109 (41), 58 (bp).

Example 7

3-(2,3-difluorophenyl)-1-ethylazetidin-3-ol-1-oxide

To a stirred solution of 3-(2,3-difluorophenyl)-1-ethylazetidin-3-ol (0.622 g, 2.91 mmol) in dichloromethane (30 mL) was added 3-chloroperoxybenzoic acid in portions (77%, 0.98 g, 4.37 mmol). The resulting mixture was stirred at ambient temperature for 5 h. The reaction mixture was poured onto a column of basic alumina, the column was washed with dichloromethane and eluated with methanol. Purification by HPLC on waters OBD C18, 5 µm (MeOH/33 mM NH3, 10:90 to 30:70) gave the title compound (0.160 g, 23.9%). The N-oxide was converted to the hydrochloric acid salt and recrystallized from methanol/acetonitrile. The product was analyzed by LCMS (Qtrap, Applied Biosystems, Q1 MS): MS (m+1)/z; 231 (M+1, bp).

Example 8

3-(2,3-difluorophenyl)-3-methoxyazetidine

To a stirred solution of tert-butyl 3-(2,3-difluorophenyl)-3-methoxyazetidine-1-carboxylate (0.7 g, 2.34 mmol) in dichloromethane (20 mL) was added trifluoroacetic acid (3 ml, 40 mmol). The resulting mixture was stirred at ambient temperature for 2 h. The solvent was evaporated and the crude product was purified on a Biotage Isolute SCX-3 SPE column (washed with methanol and eluted with methanol/triethylamine, 4:1). The solvents where evaporated to give (0.16 g, 64%) of the title compound. The amine was converted to the oxalic acid salt and recrystallized from ethanol/diethyl ether/diisopropyl ether: M.p. 141-142° C. MS m/z (relative intensity, 70 eV) 199 (M+, 1), 170 (bp), 169 (97), 140 (82), 127 (47).

Example 9

3-(2,3-difluorophenyl)-1-ethyl-3-methoxyazetidine

A mixture of 3-(2,3-difluorophenyl)-3-methoxyazetidine (0.75 g, 4.05 mmol), potassium carbonate (0.99 g, 8.1 mmol) and iodoethane (0.388 ml, 4.05 mmol) in acetonitrile (25 ml) was stirred at ambient temperature for 1 h. Water (50 mL) and ethyl acetate (50 mL) was added, the organic phase was collected and the aqueous phase was extracted with ethyl acetate (2×50 ml). The combined organic phase was dried (Na$_2$SO$_4$), filtered and evaporated to dryness. The crude product was purified by flash column chromatography on silica gel (ethyl acetate/methanol 1:1) to give the title compound (0.58 g, 63%). The amine was converted to the oxalic acid salt and recrystallized from ethanol/diethyl ether/diisopropyl ether: M.p. 147-148° C. MS m/z (relative intensity, 70 eV) 227 (M+, 4), 170 (66), 169 (bp), 140 (63), 127 (39).

Example 10

3-(2,3-difluorophenyl)-1-(ethyl-D5)azetidin-3-ol

A mixture of 3-(2,3-difluorophenyl)azetidin-3-ol (0.025 g, 0.135 mmol), 1-Iodoethane-D5 (0.0108 ml, 0.135 mmol) and potassium carbonate (0.0373, 0.27 mmol) in acetonitrile (5 ml) was heated with microwave irradiation at 110° C. for 10 min. The crude product was analyzed by GCMS. Analysis showed ~90% conversion. MS m/z (relative intensity, 70 eV) 218 (M+, 1), 156 (22), 141 (43), 127 (35), 63 (bp).

Preparation 1

1,3-dichloro-2-(2,3-difluorophenyl)propan-2-ol

To a solution of 1-bromo-2,3-difluorobenzene (19.5 g, 0.10 mol) in dry diethyl ether (120 mL), under nitrogen at −78° C., was added dropwise, n-hexyllithium (2.3 M in hexane, 41.7 ml, 0.096 mol). The mixture was stirred for 1 min after which a solution of 1,3-dichloroacetone (12.2 g, 0.096 mol) in dry diethyl ether (30 mL) was added dropwise. The resulting mixture was stirred at −78° C. for 1 h and then brought to ambient temperature and stirred for 1 h. Aqueous hydrochloric acid (50 mL. 10%) was added and the mixture was extracted with ethylacetate (2×50 ml). The combined organic phase was washed with brine, dried (Na$_2$SO$_4$), filtered and evaporated to dryness. The crude product was purified by flash column chromatography on silica gel (ethylacetate/isooctane, 1:9 to 1:1) to give the title compound (11.8 g, 48%). MS m/z (rel. intensity, 70 eV) 241 (M+, 1), 193 (33), 191 (bp), 141 (11), 127 (68).

Preparation 2 tert-butyl 3-(3,4-difluorophenyl)-3-hydroxyazetidine-1-carboxylate

To a solution of 4-bromo-1,2-difluorobenzene (1.35 g, 7.01 mmol) in dry diethylether (50 ml) at −78° C. under nitrogen was added n-hexyllithium (2.3 M in hexane, 3.0 ml, 7.01 mmol) dropwise. The mixture was stirred for 10 min after which a solution of 1-Boc-azetidone (1.0 g, 5.85 mmol) in dry diethyl ether (10 mL) was added dropwise. The resulting mixture was stirred at −78° C. for 10 min and then brought to ambient temperature and stirred for 10 min. Saturated aqueous ammonium chloride (50 mL,) was added and the mixture was extracted with tert-butyl methyl ether (2×50 ml). The combined organic phase was dried (Na$_2$SO$_4$), filtered and evaporated to dryness. The crude product was purified by flash column chromatography on silica gel (ethylacetate/isooctane 1:1) to give the title compound (1.06 g). MS m/z (rel. intensity, 70 eV) 285 (M+, 1), 156 (60), 141 (43), 127 (80), 57 (bp).

Preparation 3

3-(3,4-difluorophenyl)azetidin-3-ol

A mixture of tert-butyl 3-(3,4-difluorophenyl)-3-hydroxyazetidine-1-carboxylate (1.06 g, 3.72 mmol) and trifluoroacetic acid (3 ml) in dichloromethane (30 ml) was stirred at ambient temperature for 1.5 h. The solvent was evaporated and the crude product was purified on a Biotage Isolute SCX-3 SPE column (washed with methanol and eluted with methanol/triethylamine, 4:1) to give the title compound (0.52 g). MS m/z (rel. intensity, 70 eV) 185 (M+, 1), 156 (50), 141 (bp), 127 (58), 114 (90).

Preparation 4

1,3-dichloro-2-(3,5-difluorophenyl)propan-2-ol

A mixture of 1-bromo-3,5-difluorobenzene (5.0 g, 25.9 mmol), magnesium turnings (0.82 g, 31.1 mmol) and a small piece of iodine in dry tetrahydrofuran (50 mL) under nitrogen was stirred for 1 h at ambient temperature after which a solution of 1,3-dichloroacetone (3.46 g, 25.9 mmol) in dry tetrahydrofuran (20 mL) was added dropwise. The resulting mixture was stirred at ambient temperature for 1 h. Aqueous hydrochloric acid (50 ml, 5%) was added and the phases were separated and the aqueous phase was extracted with ethylacetate (2×50 ml). The combined organic phase was washed with brine, dried ($Na_2SO_4$), filtered and evaporated to dryness. The crude product was purified by flash column chromatography on silica gel (ethylacetate/isooctane, 1:9 to 1:1) to give the title compound (2.78 g, 45%). MS m/z (rel. intensity, 70 eV) 241 (M+, 1), 193 (32), 191 (bp), 127 (68), 77 (39).

Preparation 5 tert-butyl 3-(3-chloro-5-fluorophenyl)-3-hydroxyazetidine-1-carboxylate

A mixture of 1-bromo-3-chloro-5-fluorobenzene (1.47 g, 7.01 mmol), magnesium turnings (0.82 g, 31.1 mmol) and a small piece of iodine in dry tetrahydrofuran (50 mL), under nitrogen was gently heated until reaction started and stirred for 1 h at ambient temperature after which a solution of 1-Boc-3-azetidinone (1.0 g, 5.85 mmol) in dry diethyl ether (10 mL) was added dropwise. The resulting mixture was stirred for 15 min and water (70 ml) and saturated aqueous ammonium chloride (20 mL) was added and the mixture was extracted with ethyl acetate (2×50 ml). The combined organic phase was dried ($Na_2SO_4$), filtered and evaporated to dryness. The crude product was purified by flash column chromatography on silica gel (ethylacetate/isooctane 1:4 to 1:1) to give the title compound (1.25 g). MS m/z (rel. intensity, 70 eV) 285 (M+, 1), 156 (60), 141 (43), 127 (80), 57 (bp).

Preparation 6

3-(3-chloro-5-fluorophenyl)azetidin-3-ol

A mixture of tert-butyl 3-(3-chloro-5-fluorophenyl)-3-hydroxyazetidine-1-carboxylate (1.25 g, 4.14 mmol) and trifluoroacetic acid (3 ml) in dichloromethane (50 ml) was stirred at ambient temperature for 1 h. The solvent was evaporated and the crude product was purified on a Biotage Isolute SCX-3 SPE column (washed with methanol and eluted with methanol/triethylamine, 4:1) to give the title compound (0.74 g). MS m/z (rel. intensity, 70 eV) 201 (M+, 1), 172 (47), 157 (53), 130 (76), 109 (bp).

Preparation 7

1,3-dichloro-2-(3-chloro-2-fluorophenyl)propan-2-ol

To a solution of 1-bromo-3-chloro-2-fluorobenzene (1.4 g, 6.7 mmol) in dry diethyl ether (25 mL), at −78° C. under nitrogen was added n-hexyllithium (2.5 M in hexane, 3.2 ml, 8.0 mmol) dropwise. The mixture was stirred for 10 min after which a solution of 1,3-dichloroacetone (1.1 g, 7.3 mmol) in dry diethyl ether (10 ml) was added dropwise. The resulting mixture was stirred at −78° C. for 0.5 h and then brought to ambient temperature and stirred for 2 h. Aqueous saturated ammonium chloride (25 ml) was added and the mixture was extracted with ethylacetate (3×25 ml). The combined organic phase was dried ($Na_2SO_4$) and evaporated to dryness. The crude product was purified by flash column chromatography on silica gel (ethylacetate/isooctane, 1:9 to 1:1) to give the title compound (0.88 g, 51%). MS m/z (rel. intensity, 70 eV) 257 (M+, 1), 209 (64), 207 (bp), 143 (44), 77 (13).

Preparation 8 tert-butyl 3-(2,3-difluorophenyl)-3-hydroxyazetidine-1-carboxylate

To a solution of 3-bromo-1,2-difluorobenzene (2.3 g, 11.8 mmol) in dry diethylether (20 ml) at −78° C., under nitrogen was added n-butyllithium (2.5 M in hexane, 4.7 ml, 11.8 mmol) dropwise. The mixture was stirred for 1 h after which a solution of 1-Boc-3-azetidinone (2.0 g, 11.7 mmol) in dry diethyl ether (20 mL) was added dropwise. The resulting mixture was stirred at −78° C. for 15 min and then brought to ambient temperature and stirred for 2 h. Aqueous ammonium chloride (50 mL, 50%) and diethylether was added, the organic phase was collected and the aqueous phase was extracted with ethyl acetate (2×50 ml). The combined organic phase was dried ($Na_2SO_4$), filtered and evaporated to dryness. The crude product was purified by flash column chromatography on silica gel (ethylacetate/isooctane 1:4 to 1:1) to give the title compound (1.9 g). MS m/z (rel. intensity, 70 eV) 285 (M+, 1), 156 (55), 141 (69), 127 (bp), 57 (88).

Preparation 9

3-(2,3-difluorophenyl)azetidin-3-ol

Trifluoroacetic acid (2 ml) was added to a solution of tert-butyl 3-(2,3-difluorophenyl)-3-hydroxyazetidine-1-carboxylate (0.80 g, 2.80 mmol) in dichloromethane (30 ml). The reaction mixture was stirred at ambient temperature for 1 h. The solvent was evaporated and the crude product was purified on a Biotage Isolute SCX-3 SPE column (washed with methanol and eluted with methanol/triethylamine, 4:1) to give the title compound (0.52 g). MS m/z (rel. intensity, 70 eV) 185 (M+, 1), 141 (68), 127 (bp), 114 (82), 63 (40).

Preparation 10 tert-butyl 3-(2,3-difluorophenyl)-3-methoxyazetidine-1-carboxylate

To a solution of tert-butyl 3-(2,3-difluorophenyl)-3-hydroxyazetidine-1-carboxylate (1.1 g, 3.86 mmol) in N,N-dimethylformamide (15 mL), was added sodium hydride (60% dispersion in mineral oil, 0.31 g, 7.7 mmol). The mixture was stirred for 20 min and methyliodide (0.29 mL, 4.63 mmol) was added. The mixture was stirred for 30 min, aqueous lithium chloride (50 ml, 5%) was added and the aqueous phase was extracted with ethyl acetate (2×50 mL). The combined organic phase was dried ($Na_2SO_4$), filtered and evaporated to give the title compound (1.55 g). MS m/z (rel. intensity, 70 eV) 299 (M+, 1), 223 (21), 169 (62), 140 (49), 57 (bp).

Preparation 11

1,3-dichloro-2-(3,4-difluorophenyl)propan-2-ol

Preparation according to Preparation 1: 1-bromo-3,4-difluorobenzene (5 g, 25.9 mmol), dry diethyl ether (100 mL), n-hexyllithium (2.3 M in hexane, 11.2 ml, 25.9 mmol) and 1,3-dichloroacetone (3.29 g, 25.9 mol). Yield: 4.54 g (73%). MS m/z (rel. intensity, 70 eV) 241 (M+, 1), 193 (32), 191 (bp), 141 (14), 127 (64).

Preparation 12

1,3-dichloro-2-(3-chloro-5-fluorophenyl)propan-2-ol

Preparation according to Preparation 1: 1-bromo-3-chloro-5-fluorobenzene (5 g, 23.9 mmol), dry diethyl ether (100 mL), n-hexyllithium in hexane (2.3 M, 10.4 ml, 23.9 mmol) and 1,3-dichloroacetone (3.03 g, 23.9 mol). Yield: 4.49 g (73%). MS m/z (rel. intensity, 70 eV) 257 (M+, 1), 209 (65), 207 (bp), 211 (11), 143 (28).

Preparation 13 tert-butyl 3-(2,3-difluorophenyl)-3-methoxyazetidine-1-carboxylate

Tert-butyl 3-(2,3-difluorophenyl)-3-hydroxyazetidine-1-carboxylate (0.7 g, 2.45 mmol) was dissolved in N,N-dimethylformamide (20 mL) and sodium hydride (60% dispersion in mineral oil, 0.2 g, 4.90 mmoL) was added at 0° C. The mixture was stirred at 0° C. for 15 min and at ambient temperature for 20 min after which methyliodide (0.41 mL, 2.94 mmol) was added. The mixture was stirred for 1 h at ambient temperature, a mixture of aqueous lithium chloride (5%, aq, 20 mL) and ethyl acetate (20 ml) was added and the organic phase was collected. The aqueous phase was extracted with ethyl acetate (2×20 mL) and the combined organic phase was dried ($Na_2SO_4$), filtered and evaporated. Purification by flash column chromatography on silica gel (ethyl acetate/isooctane 2:8 to 1:1) gave the title compound (0.7 g, 95%). MS m/z (rel. intensity, 70 eV) 299 (M+, 1), 223 (60), 198 (35), 169 (bp), 170 (bp).

Example 11

Biological Activity

The following tests were used for evaluation of the compounds according to the invention.

In Vivo Test: Behaviour

Behavioural activity was measured using eight Digiscan activity monitors (RXYZM (16) TAO, Omnitech Electronics, Columbus, Ohio, USA), connected to an Omnitech Digiscan analyzer and an Apple Macintosh computer equipped with a digital interface board (NB D10-24, National Instruments, USA). Each activity monitor consisted of a quadratic metal frame (W×L=40 cm×40 cm) equipped with photobeam sensors. During measurements of behavioural activity, a rat was put in a transparent acrylic cage (W×L×H, 40×40×30 cm) which in turn was placed in the activity monitor. Each activity monitor was equipped with three rows of infrared photobeam sensors, each row consisting of 16 sensors. Two rows were placed along the front and the side of the floor of the cage, at a 90° angle, and the third row was placed 10 cm above the floor to measure vertical activity. Photobeam sensors were spaced 2.5 cm apart. Each activity monitor was fitted in an identical sound and light attenuating box containing a weak house light and a fan.

The computer software was written using object oriented programming (LabVIEW®, National instruments, Austin, Tex., USA).

Behavioural data from each activity monitor, representing the position (horizontal center of gravity and vertical activity) of the animal at each time, were recorded at a sampling frequency of 25 Hz and collected using a custom written LABView™ application. The data from each recording session were stored and analyzed with respect to distance traveled. Each behavioural recording session lasted 60 min, starting approximately 4 min after the injection of test compound. Similar behavioural recording procedures were applied for drug-naïve and drug pre-treated rats. Rats pre-treated with d-amphetamine were given a dose of 1.5 mg/kg i.p. 10 min before the recording session in the activity monitor. Rats pre-treated with MK-801 were given a dose of 0.7 mg/kg i.p. 90 min before the recording session in the activity monitor. The results are presented as counts/60 minutes, or counts/30 minutes, in arbitrary length units. Statistical comparisons were carried out using Student's t-test against the control group. In MK-801 or amphetamine pre-treated animals, statistical comparisons were made against the MK801 or d-amphetamine controls, respectively.

$ED_{50}$ values for reduction of amphetamine-induced hyperlocomotion are calculated by curve fitting. For most compounds, the evaluation is based on 16 amphetamine pre-treated animals over the dose range 0, 11, 33 and 100 µmol/kg s.c. in one single experiment, with complementary doses in separate experiments. Calculations are based on distance during the last 45 minutes of one hour of measurement. The distances are normalised to amphetamine-control and fitted by least square minimization to the function "End-(End-Control)/(1+(dose/$ED_{50}$)$^{Slope}$)". The four parameters (Control, End, $ED_{50}$ and Slope) are fitted with the restrictions: $ED_{50}$>0, 0.5<Slope<3, End=0% of control. The restriction with locked End is made to focus on potency rather than efficacy. To estimate confidence levels for the parameters, the fit is repeated 100 times with a random evenly distributed squared weight (0 to 1) for every measurement value. Presented $ED_{50}$-ranges cover 95% of these values.

In vivo Test: Neurochemistry

After the behavioural activity sessions, the rats were decapitated and their brains rapidly taken out and put on an ice-cold petri-dish. The limbic forebrain, the striatum, the frontal cortex and the remaining hemispheral parts of each rat were dissected and frozen. Each brain part was subsequently analyzed with respect to its content of monoamines and their metabolites.

The monoamine transmitter substances (NA (noradrenaline), DA (dopamine), 5-HT (serotonin)) as well as their amine (NM (normethanephrine), 3-MT (3-methoxytyramine)) and acid (DOPAC (3,4-dihydroxyphenylacetic acid), 5-HIAA (5-hydroxyindoleacetic acid), HVA (homovanillic acid)) metabolites are quantified in brain tissue homogenates by HPLC separations and electrochemical detection.

The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18(2), dp 3 µm, 50*2 mm i.d., Phenomenex) and electrochemical detection is accomplished at two potentials on glassy carbon electrodes (MF-1000, Bioanalytical Systems, Inc.). The column effluent is passed via a T-connection to the detection cell or to a waste outlet. This is accomplished by two solenoid valves, which block either the waste or detector outlet. By preventing the chromatographic front from reaching the detector, better detection conditions are achieved. The aqueous mobile phase (0.4 ml/min) for the acid system contains citric acid 14 mM, sodium citrate 10 mM, MeOH 15% (v/v) and EDTA 0.1 mM. Detection potentials relative to Ag/AgCl reference are 0.45 and 0.60V. The aqueous ion pairing mobile phase (0.5 ml/min) for the amine system contains citric acid 5 mM, sodium citrate 10 mM, MeOH 9% (v/v), MeCN 10.5% v/v), decane sulfonic acid 0.45 mM, and EDTA 0.1 mM. Detection potentials relative to Ag/AgCl reference are 0.45 and 0.65V.

$ED_{50}$ values for the increase of DOPAC in striatum are calculated by curve fitting. For most compounds, the evaluation is based on 20 animals over the dose range 0, 3.7, 11, 33 and 100 μmol/kg s.c. in one single experiment, with complementary doses in separate experiments. The DOPAC levels are normalised to control and fitted by least square minimization to the function "End-(End-Control)/(1+(dose/$ED_{50}$)$^{Slope}$)". The four parameters (Control, End, $ED_{50}$ and Slope) are fitted with the restrictions: $ED_{50}$>0, 0.5<Slope<3, 350<End<400% of control. To estimate confidence levels for the parameters, the fit is repeated 100 times with a random evenly distributed squared weight (0 to 1) for every measurement value. Presented $ED_{50}$-ranges cover 95% of these values.

In vivo Test: Oral Bioavailability

Experiments are performed 24 hours after implantation of arterial and venous catheters. Test compound is administered orally at 12.5 μmol/kg or intravenously at 5 μmol/kg using the venous catheters, n=3 per group. Arterial blood samples are then taken during six hours at 0, 3, 9, 27, 60, 120, 180, 240, 300 and, 360 minutes after administration of the test compound. The oral bioavailability was calculated as the ratio of the AUC (Area under curve) obtained after oral administration over the AUC obtained after intravenous administration for each rat. The parameter AUC was calculated according to the following:

AUC: the area under the plasma concentration versus time curve from time zero to the last concentration measured (Clast), calculated by the log/linear trapezoidal method.

The levels of test compound are measured by means of liquid chromatography-mass spectrometry (LC-MS) (Hewlett-Packard 1100MSD Series). The LC-MS module includes a quaternary pump system, vacuum degasser, thermostatted autosampler, thermostatted column compartment, diode array detector and API-ES spray chamber. Data handling was performed with a HP ChemStation rev.A.06.03. system. Instrument settings:MSD mode: Selected ion monitoring (SIM) MSD polarity: Positiv Gas temp: 350° C. Drying gas: 13.0 l/min Nebulizer gas: 50 psig Capillary voltage: 5000 V Fragmentor voltage: 70 V Analytical column: Zorbax eclipse XDB-C8 (4.6*150 mm, 5 μm) at 20° C. The mobile phase was acetic acid (0.03%) (solvent A) and acetonitrile (solvent B). The flow rate of the mobile phase was 0.8 ml/min. The elution was starting at 12% of solvent β isocratic for 4.5 min, then increasing linearity to 60% over 4.5 min.

Extractions procedure: Plasma samples (0.25-0.5 ml) were diluted with water to 1 ml, and 60 pmol (100 μl) internal standard (−)-OSU6241 was added. The pH was adjusted to 11 by the addition of 25 μl saturated $Na_2CO_3$. After mixing, the samples were extracted with 4 ml dichloromethane by shaking for 20 min. The organic layer was after centrifugation transferred to a smaller tube and evaporated to dryness under a stream of nitrogen. The residue was then dissolved in 120 μl mobile phase (acetic acid (0.03%): acetonitrile, 95:5) for LC-MS analysis (10 μl injected). The selective ion ($MH^+$) was monitored for each Example, and $MH^+$ 296 for (−)-OSU6241 ((3-[3-(ethylsulfonyl)phenyl]-1-propylpiperidine).

A standard curve over the range of 1-500 pmol is prepared by adding appropriate amounts of test compound to blank plasma samples.

In vitro Test: Metabolic Stability in Rat Liver Microsomes

Rat liver microsomes were isolated as described by Förlin L, 1980, with minor modifications e.g. 3 mL/g liver of a 0.1 M $Na/K^*PO_4$ buffer with 0.15M KCl, pH 7.4, (buffer 1) was added before homogenisation, the homogenate was centrifuged for 20 minutes instead of 15, the supernatant was ultracentrifuged at 100.000 g instead of 105.000 g and the pellet from the ultracentrifugation was resuspended in 1 mL/g liver of 20% v/v 87% glycerol in buffer 1.

1 μL of, 0.2 or 1 mM test substance diluted in water, and 10 μL 20 mg/mL rat liver microsome were mixed with 149 μL 37° C. buffer 1 and the reaction was started by addition of 40 μL 4.1 mg/mL NADPH. After 0 or 15 minutes incubation at 37° C. in a heating block (LAB-LINE, MULTI-BLOK Heater or lab4you, TS-100 Thermo shaker at 700 rpm) the reaction was stopped by addition of 100 μL pure acetonitrile. The protein precipitation was then removed by rejecting the pellet after centrifugation at 10.000 g for 10 minutes (Heraeus, Biofuge fresco) in 4° C. The test compound was analysed using HPLC-MS (Hewlett-Packard 1100MSD Series) with a Zorbax SB-C18 column (2.1*150 mm, 5 μm) using 0.03% formic acid and acetonitrile as mobile phase (gradient) or a Zorbax Eclipse XDB-C18 (3*75 mm, 3.5 μm) using 0.03% acetic acid and acetonitrile as mobile phase (gradient). The 15 min turnover was calculated as the fraction of test compound eliminated after 15 minutes, expressed in percent of 0 min levels, i.e. 100*[conc test compound at 0 min−concentration at 15 min]/conc at 0 min.

Preparation of liver microsomes was performed as described in Förlin, 1980. Protocols for incubation with liver microsomes are referred in Crespi & Stresser, 2000, and Renwick et al., 2001.

Microdialysis

Male Sprague-Dawley rats weighing 220-320 g were used throughout the experiments. Before the experiment the animals were group housed, five animals in each cage, with free access to water and food. The animals were housed at least one week after arrival prior to surgery and use in the experiments. Each rat was used only once for microdialysis.

We use a modified version (Waters et al., 1994) of the I-shaped probe (Santiago and Westerink, 1990). The dialysis membrane we use is the AN69 poly-acrylonitrile/sodium-methalylsulfonate copolymer (HOSPAL; o.d./i.d. 310/220 μm: Gambro, Lund, Sweden). In the dorsal striatum we use probes with an exposed length of 3 mm of dialysis membrane and in the prefrontal cortex the corresponding length is 2.5 mm. The rats were operated under isoflurane inhalationanesthesia while mounted into a Kopf stereotaxic instrument. Co-ordinates were calculated relative to bregma; dorsal striatum AP +1, ML ±2.6, DV −6.3; Pf cortex, AP +3.2, 8° ML ±1.2, DV −4.0 according to (Paxinos & Watson, 1986). The dialysis probe was positioned in a burr hole under stereotaxic guidance and cemented with phosphatine dental cement.

The rats were housed individually in cages for 48 h before the dialysis experiments, allowing them to recover from surgery and minimizing the risk of drug interactions with the anaesthetic during the following experiments. During this period the rats had free access to food and water. On the day of experiment the rats were connected to a micro perfusion pump via a swiwel and were replaced in the cage where they could move freely within its confinements. The perfusion medium was a Ringer's solution containing in mmol/l: NaCl; 140, CaCl2; 1.2, KCl; 3.0, MgCl2; 1.0 and ascorbic acid; 0.04 according to (Moghaddam & Bunney, 1989). The pump was set to a perfusion speed of 2 μl/min and 40 μl samples were collected every 20 min. Each sample was analyzed at two HPLC systems. On an autoinjector (CMA 200) with a 10-port valve (Valco C10WE), holding two sample loops in series (4 μl and 20 μl), each brain dialysate sample is loaded in both loops simultaneously. At injection the 20 μl sample is introduced into a column switching system (reverse-phase combined with reverse-phase ion-pairing) for dopamine (DA), noradrenaline (NA), normetanephrine (NM), 3-methoxytyramine (3-MT) and serotonin (5-hydroxytryptamine, 5-HT) determination, while the 4 μl sample is introduced on a reverse-phase column for the chromatography of the acidic monoamine metabolites 3,4-di-hydroxyphenylacetic acid (DOPAC), homovanillic acid (HVA) and 5-hydroxyindoleacetic acid (5-HIAA). The currents generated by the two EC detectors are converted to digital data and evaluated using Chromeleon software (Dionex) on a PC. The method sample turn over time was 4.5 min and two parallel experiments are normally analyzed simultaneously on the system.

After the experiment the rats were uncoupled from the perfusion pump and decapitated. Their brains were rapidly taken out and fixed in Neo-fix solution (Kebolab, Sweden) for subsequent inspection of probe localisation. The Animal Ethics Committee in Göteborg, Sweden approved the procedures applied in these experiments.

The results of these experiments are presented in Table 1 below.

TABLE 1

Maximum effect compared to baseline values (percent of control ± SEM) at 50 μmol/kg s.c.

| Compound | NA Stri ± SEM | DA Stri ± SEM | 5-HT Stri ± SEM | NA PFC ± SEM | DA PFC ± SEM | 5-HT PFC ± SEM |
|---|---|---|---|---|---|---|
| Example 1 | 261 ± 151 | 219 ± 113 | 113 ± 13 | 438 ± 91 | 211 ± 61 | 130 ± 11 |
| Example 2 | — | 112 | 162 | 397 ± 59 | 309 ± 62 | 182 ± 33 |
| Example 9 | — | 122 ± 12 | 134 ± 22 | 298 ± 79 | 215 ± 54 | 169 ± 65 |

The microdialysis was performed in awake and freely moving rats.
Dopamine = DA; Norepinephrine = NA; Serotonin = 5-HT; Stri = Striatum; PFC = Prefrontal Cortex.

The microdialysis was performed in awake and freely moving rats.

Dopamine=DA; Norepinephrine=NA; Serotonin=5-HT; Stri=Striatum; PFC=Prefrontal Cortex.

REFERENCES

Crespi C L and D M Stresser: Fluorometric screening for metabolism based drug-drug interactions. *J. Pharm. Tox. Meth.* 2000 44 325-331;

Förlin L: Effects of Clophen A50, 3-methylcholantrene, pregnenolone-16aq-carbonitrile and Phenobarbital on the hepatic microsomal cytochrome P-450-dependent monooxygenaser system in rainbow trout, salmo gairdneri, of different age and sex. *Tox. Appl. Pharm.* 1980 54 (3) 420-430;

Renwick A B et al.: Metabolism of 2,5-bis(trifluoromethyl)-7-benzyloxy-4-trifluoromethylcoumarin by human hepatic CYP isoforms: evidence for selectivity towards CYP3A4. *Xenobiotica* 2001 31 (4) 187-204;

Moghaddam B & Bunney B S: Ionic Composition of Microdialysis Perfusing Solution Alters the Pharmacological Responsiveness and Basal Outflow of Striatal Dopamine. *J. Neurochem.* 1989 53 652-654;

Paxinos G & Watson C: The Rat Brain in Stereotaxic Coordinates. New York, Academic Press, 1986.

Santiago M & Westerink B H C: Characterization of the in vivo release of dopamine as recorded by different types of intracerebral microdialysis probes. *Naunyn-Schmiedeberg's Arch. Pharmacol.* 1990 342 407-414;

Waters N, Lofberg L, Haadsma-Svensson S, Svensson K, Sonesson C and Carlsson A: Differential effects of dopamine D2 and D3 receptor antagonists in regard to dopamine release, in vivo receptor displacement and behaviour. *J. Neural. Transm. Gen. Sect.* 1994 98 (1): 39-55.

The invention claimed is:
1. A 3-phenyl-azetidine derivative of Formula (1):

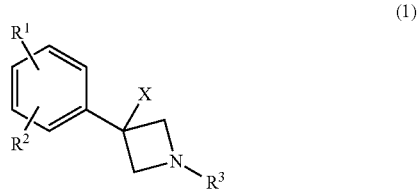

any of its stereoisomers or any mixture of its stereoisomers, or an N-oxide thereof, or a deuterated analog thereof, or a pharmaceutically acceptable salt thereof, wherein
X is OH or OCH$_3$;
R$^1$ is F or Cl;
R$^2$ is H, F or Cl;
R$^3$ is H, CH$_3$ and CH$_2$CH$_3$;
and with the proviso that if X is OH, then R$^3$ is not H.

2. The 3-phenyl-azetidine derivative according to claim 1, any of its stereoisomers or any mixture of its stereoisomers, or an N-oxide thereof, or a deuterated analog thereof, or a pharmaceutically acceptable salt thereof, wherein X is OH or OCH$_3$.

3. The 3-phenyl-azetidine derivative according to claim 1, any of its stereoisomers or any mixture of its stereoisomers, or an N-oxide thereof, or a deuterated analog thereof, or a pharmaceutically acceptable salt thereof, wherein R$^1$ is F or Cl.

4. The 3-phenyl-azetidine derivative according to claim 1, any of its stereoisomers or any mixture of its stereoisomers, or an N-oxide thereof, or a deuterated analog thereof; or a pharmaceutically acceptable salt thereof, wherein R$^2$ is H, F or Cl.

5. The 3-phenyl-azetidine derivative according to claim 1, any of its stereoisomers or any mixture of its stereoisomers, or an N-oxide thereof; or a deuterated analog thereof, or a pharmaceutically acceptable salt thereof, wherein R$^3$ is H, CH$_3$ or CH$_2$CH$_3$, or a deuterated analog thereof.

6. The 3-phenyl-azetidine derivative according to claim 1, which is
3-(2,3-Difluorophenyl)-1-ethylazetidin-3-ol ;
3-(3,4-Difluorophenyl)-1-ethylazetidin-3-ol;
3-(3,5-Difluorophenyl)-1-ethylazetidin-3-ol;
3-(3-Chloro-5fluorophenyl)-1-ethylazetidin-3-ol;
3-(3,4-Difluorophenyl)-1-(ethyl-D5)azetidin-3-ol;
3-(3-Chloro-2-fluorophenyl)-1 -ethylazetidin-3-ol;
3-(2,3-Difluorophenyl)-1-ethylazetidin-3-ol1-oxide;
3-(2,3-Difluorophenyl)-3-methoxyazetidine;
3-(2,3-Difluorophenyl)-1-ethyl-3-methoxyazetidine; or
3-(2,3-Difluorophenyl)-1-(ethyl-D5)azetidin-3-ol;

any of its stereoisomers or any mixture of its stereoisomers, or an N-oxide thereof, or a deuterated analog thereof or a pharmaceutically acceptable salt thereof.

7. A pharmaceutical composition, comprising a therapeutically effective amount of a 3-phenyl-azetidine derivative of claim 1, any of its stereoisomers or any mixture of its stereoisomers, or an N-oxide thereof, or a deuterated analog thereof; or a pharmaceutically acceptable salt thereof, together with at least one pharmaceutically acceptable carrier, excipient or diluent.

8. A method for treatment or alleviation of a disease or a disorder or a condition of a living animal body, including a human, which disorder, disease or condition is responsive to modulation of catecholamines in the cerebral cortex, which method comprises the step of administering to such a living animal body in need thereof a therapeutically effective amount of a 3-phenyl-azetidine derivative according to claim 1, or any of its stereoisomers or any mixture of its stereoisomers, or an N-oxide thereof, or a deuterated analog thereof, or a pharmaceutically acceptable salt thereof.

9. The method according to claim 8, wherein the disease, disorder or condition is dementia, age-related cognitive impairment, Autism spectrum disorders, ADHD, Cerebral Palsy, Huntington's disease, Gilles de la Tourette's syndrome, depression, bipolar disorder, schizophrenia, schizophreniform disorders, generalized anxiety disorder (GAD), specific phobias, panic disorder, sleep disorders, bipolar disorders, drug induced psychotic disorders, iatrogenic psychoses, Iatrogenic hallucinoses, non-iatrogenic psychoses, non-iatrogenic hallucinoses, mood disorders, anxiety disorders, depression, obsessive-compulsive disease, emotional disturbances related to ageing, Alzheimer's disease, dementia, dementia disorders related to Alzheimer's disease, age-related cognitive impairment, brain injury, substance abuse, disorders characterized by misuse of food, sleep disorders, sexual disorders, eating disorders, obesity, headaches, pains in conditions characterized by increased muscular tone, movement disorders, Parkinson's disease, Parkinsonism, parkinsonian syndromes, dyskinesias, L-DOPA induced dyskinesias, dystonias, neurodevelopmental disorders, neurodegenerative disorders, tics, tremor, restless legs, narcolepsy or behavioural disorders.

10. The method according to claim 9, wherein the disease, disorder or condition is dementia, age-related cognitive impairment, Autism spectrum disorders, ADHD, Cerebral Palsy, Huntington's disease, Gilles de la Tourette's syndrome, depression, bipolar disorder, schizophrenia, schizophreniform disorders, generalized anxiety disorder (GAD), specific phobias, panic disorder, sleep disorders, bipolar disorders, Alzheimer's disease, or L-DOPA induced dyskinesias.

11. The 3-phenyl-azetidine derivative according to claim 1, which is 3-(2,3-difluorophenyl)-1-ethylazetidin-3-ol.

* * * * *